(12) United States Patent
Mechoulam et al.

(10) Patent No.: US 7,759,526 B2
(45) Date of Patent: Jul. 20, 2010

(54) PHARMACEUTICAL COMPOSITIONS COMPRISING CANNABIDIOL DERIVATIVES

(75) Inventors: Raphael Mechoulam, Jerusalem (IL); Susana Tchilibon, Jerusalem (IL); Ester Fride, Efrat (IL); Lumir Hanus, Jerusalem (IL); Aviva Breuer, Jerusalem (IL); Ruth Gallily, Jerusalem (IL)

(73) Assignee: Yissum Research Development Company, Jerusalem (IL)

( * ) Notice: Subject to any disclaimer, the term of this patent is extended or adjusted under 35 U.S.C. 154(b) by 1961 days.

(21) Appl. No.: 10/311,554

(22) PCT Filed: Jun. 12, 2001

(86) PCT No.: PCT/IL01/00537

§ 371 (c)(1),
(2), (4) Date: Jan. 30, 2003

(87) PCT Pub. No.: WO01/95899

PCT Pub. Date: Dec. 20, 2001

(65) Prior Publication Data

US 2003/0166727 A1 Sep. 4, 2003

(30) Foreign Application Priority Data

Jun. 16, 2000 (IL) .................................. 136839

(51) Int. Cl.
*C07C 43/166* (2006.01)
(52) U.S. Cl. ..................................... 568/619

(58) Field of Classification Search ........................ None
See application file for complete search history.

(56) References Cited

U.S. PATENT DOCUMENTS 3,478,029 A  11/1969  Schicke ................... 260/256.6

(Continued)

FOREIGN PATENT DOCUMENTS

| CA | 2 367 262 | 9/2000 |
| EP | 1289517 | 11/2005 |
| WO | WO 97/42938 | 11/1997 |

OTHER PUBLICATIONS

X-001076658 Samara et al Journal of Chromatography, 562 (1991) 299-322.*

(Continued)

*Primary Examiner*—Carlos A Azpuru
(74) *Attorney, Agent, or Firm*—Myers Bigel Sibley & Sajovec, PA

(57) ABSTRACT

The present invention relates to cannabidiol derivatives and to pharmaceutical compositions comprising cannabidiol derivatives being antiinflammatory agents having analgesic, antianxiety, anticonvulsive, neuroprotective, antipsychotic and anticancer activity.

The present invention also relates to a process for the preparation of cannabidiol derivatives.

It also relates to the use of cannabidiol derivatives and of pharmaceutical compositions comprising same in the preparation of a medicament, in a method of the treatment of human beings with cannabidiol derivatives or with a pharmaceutical preparations comprising same.

5 Claims, 6 Drawing Sheets

U.S. PATENT DOCUMENTS

| | | | |
|---|---|---|---|
| 5,434,295 A * | 7/1995 | Mechoulam et al. | 560/141 |
| 5,538,993 A * | 7/1996 | Mechoulam et al. | 514/454 |
| 6,235,741 B1 | 5/2001 | Bilodeau et al. | 514/257 |

OTHER PUBLICATIONS

Lander et al, Journal of the Chemical Society, Perki Transactions 1: Organic and Bio-Organic Chemistry (1972-199), 1976, (1), 8-16, Abstract.*

Green et al. 1982. Intraocular Pressure Following Systemic Administration of Cannabinoids. *Current Eye Research* 2: 247-253.

Harvey et al. 1991. Urinary Metabolites of Cannabidiol in Dog, Rat and Man and Their Identification by Gas Chromatography-Mass Spectrometry. *Journal of Chromatography* 562: 299-322.

Harvey et al. 1991. Comparative Metabolism of Cannabidiol in Dog, Rat and Man. *Pharmacology Biochemistry & Behavior* 40: 523-532.

Iversen, Leslie L., "Medical uses of marijuana?", Nature, vol. 365, Sep. 2, 1993, pp. 12-13.

* cited by examiner

PHARMACEUTICAL COMPOSITIONS COMPRISING CANNABIDIOL DERIVATIVES

This application is a 35 U.S.C. §371 national phase application filed from international application PCT/IL01/00537, filed Jun. 12, 2001, which claims priority to Israeli patent application No. 136839, filed Jun. 16, 2000. The entire contents of these applications are incorporated herein by reference in their entireties.

The present invention relates to cannabidiol derivatives and to pharmaceutical compositions comprising cannabidiol derivatives being antiinflammatory agents having analgesic, antianxiety, anticonvulsive, neuroprotective, antipsychotic and anticancer activity.

Cannabidiol (CBD, 1a) is the major non-psychotropic cannabinoid in most Cannabis preparations, such as hashish and marihuana.

CBD causes none of the psychotropic effects typical of $\Delta^9$-tetrahydrocannabinol ($\Delta^9$-THC) (Martin, Pharmacol. Rev., 38, 45-74 1986). CBD does not bind to the known cannabinoid receptors $CB_1$ or $CB_2$, and therefore does not cause the central or peripheral effects mediated by these receptors. However it has been shown in in vitro assays, in animal tests, as well as in some human, preliminary trials, to produce numerous pharmacological effects, some of which are of potential therapeutic value. Thus, recent reports describe the in vitro effects of CBD on immune cells, such as the inhibition of nitric oxide (NO) production by mouse peritoneal macrophages and the suppression of TNF, IL-1α and IFNγ by human peripheral blood mononuclear cells (Coffey et al., Intern. J. Immunopharmacol., 18, 749-752 [1996]; Watzl et al., Int. J. Immunopharmicol., 13, 1091-1093 [1991]; Srivastava et al., Immunopharmacol., 179-185 [1998]; for a review see Klein et al., Immunol. Today, 19, 373-381 [1998]) and "Malfait et al., Proc. Natl. Acad. Sci. [U.S.A.], 97, 9561-9566 [2000].". These in vitro studies lend support to earlier reports on analgesic and antiinflammatory effects in animals. Formukong et al., (Inflammation 12, 361-371 [1988]) have found that CBD is much more potent than aspirin in the phenylbenzoquinone writhing test in mice (a standard analgesic assay). In the tetradecanoylphorbolacetable (TPA) induced erythema of mouse ear (an antiinflammatory assay) CBD caused 92% inhibition of the inflammation response on application of a 100 µg/ml solution.

CBD has been found to produce several, potentially therapeutic, effects in animal models, as well as in patients with neurological diseases (for a review see Consroe, (Neurobiol. Disease, 5 534-551 [1998]), in anxiety (Guimaraes et al., Gen. Pharmacol., 25, 161-164 [1994]; Zuardi et al., Psychopharmacology [Berlin], 76, 245-250 [1982]) and in psychosis (Zuardi et al., J. Clin. Psychiatry, 56, 485-486 [1995]). Hampson et al., (Proc. Natl. Acad. Sci. USA, 95, 8268-8273 [1998]) have found that CBD is an neuroprotective antioxidant.

Surprisingly, while the enantiomeric THC's differ in their biological activity (Mechoulam et al., "Marijuana/cannabinoids: neurobiology and neurophysiology" ed. L. Murphy and A. Bartke, CRC Press, Boca Raton, Fla., pp 1-33 [1992]), both CBD enantiomers have the same anticonvulsive and certain hormonal profiles (Leite et al., Pharmacol., 124, 141-146 [1982]; Cordova et al., Psychoneuroendocrinology, 5, 53-62 [1980]). However the comparative pharmacology of CBD enantiomers has not been further explored. Also the syntheses and the pharmacology of CBD metabolites are unknown.

Said syntheses and the pharmacology have now been explored and it has surprisingly been found that compounds of general formula I

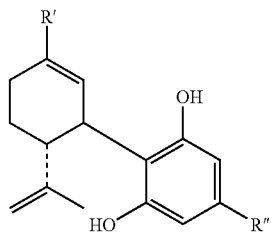

in which R' stands for COOH or $CH_2OH$; and

R" stands for
a. straight or branched alkyl of 5 to 12 carbon atoms;
b. a group —O—R"', where R"' is straight or branched alkyl of 5 to 9 carbon atoms, or a straight or branched alkyl substituted at the terminal carbon atom by a phenyl group;
c. a group —$(CH_2)_n$—O-alkyl, where n is an integer from 1 to 7 and the alkyl group contains 1 to 5 carbon atoms, and pharmaceutics compositions comprising same, are antiinflammatory agents and which have analgesic, antianxiety, anticonvulsive, neuroprotective, antipsychotic and anticancer, activity.

The present invention thus consists in pharmaceutical preparations comprising compounds of general formula I being antiinflammatory agents, which have analgesic, antianxiety, anticonvulsive, neuroprotective, antipsychotic and anticancer activity comprising as active ingredient a compound of general formula I.

The compounds of general formula I excluding those in which R" stands for $C_5H_{11}$ are novel and are within the scope of the present invention.

The pharmaceutical preparations according to the present invention may have any suitable form, e.g. be a tablet, a capsule, a granule, a suspension, a solution, etc. They may comprise in addition to the active ingredient an excipient, such as a carrier, a disintegrant, a lubricant, a stabilizer, a flavoring agent and even an other pharmaceutical effective compound.

The pharmaceutical preparations according to the present invention may be prepared by conventional methods. They comprise the various ingredients in the required amounts.

The compounds of general formula and the pharmaceutical preparations comprising same are advantageously provided to the patient in a daily dosage of the compound in between 0.01 and 20 mg/kg The present invention consists also in the use of a compound of general formula I and pharmaceutical composition comprising same in the preparation of a medicament.

The present invention also consists in a method for the treatment of human beings with a compound of general formula I or with a pharmaceutical preparation comprising same.

BRIEF DESCRIPTION OF THE DRAWINGS

FIG. 2 illustrates the effect of various doses of CBD-7-oic acid (3a) and CBD-DMH-7-oic acid (3b) and of indomethacin after arachidonic acid-induced swelling of the ear.

The present invention consists also in processes for the preparation of compounds of general formula I.

The process for the preparation of compounds of general formula I in which R'=CH$_2$OH and R"=
a. straight or branched alkyl of 5 to 12 carbon atoms;
b. a group —O—R''', where R''' is straight or branched alkyl of 5 to 9 carbon atoms, or a straight or branched alkyl substituted at the terminal carbon atom by a phenyl group;
c. a group —(CH$_2$)$_n$—O-alkyl, where n is an integer from 1 to 7 and the alkyl group contains 1 to 5 carbon atoms.

involves 8 steps starting from a compound of general formula I, in which R'=CH$_3$ and R" is one of the substituents indicated above.

The process involves blocking of the phenolic groups in order to allow further chemical transformations (step a) followed by selective epoxidation of the ring double bond (step b), selective opening of the epoxide ring to form an allylic alcohol (c), then several steps (d, e, f, g) which by allylic rearrangement lead to the dimethoxy derivative of the desired compound. The final step (h) involves demethoxylation under harsh conditions to form the desired allylic alcohol.

The specific process for the preparation of a compound of general formula I in which R stands for CH$_2$OH and R" stands for C$_5$H$_{11}$ or for 1',1'-dimethylheptyl (DMH) comprises:
a. reacting CBD or the dimethyl heptyl homologue thereof with methyliodide and potassium carbonate in DMF;
b. reacting the dimethylether obtained with 3-chlorobenzoic acid to obtain the corresponding epoxide;
c. the epoxide obtained being reacted with methyl magnesium N-cyclohexyl-isopropylamide in toluene;
d. the compound obtained in step c being acetylated;
e. the acetylate obtained being reacted with t-butyldimethylsilybromide;
f. the bromide obtained being reacted with (nBu)$_4$NH$_4$Oac in acetone to obtain the allyl acetate diether; and
g. the ether obtained being heated in a sodium hydroxide solution; and
h. the compound obtained being heated with methylmagnesium iodide to obtain the required compound.

Figure 3A:
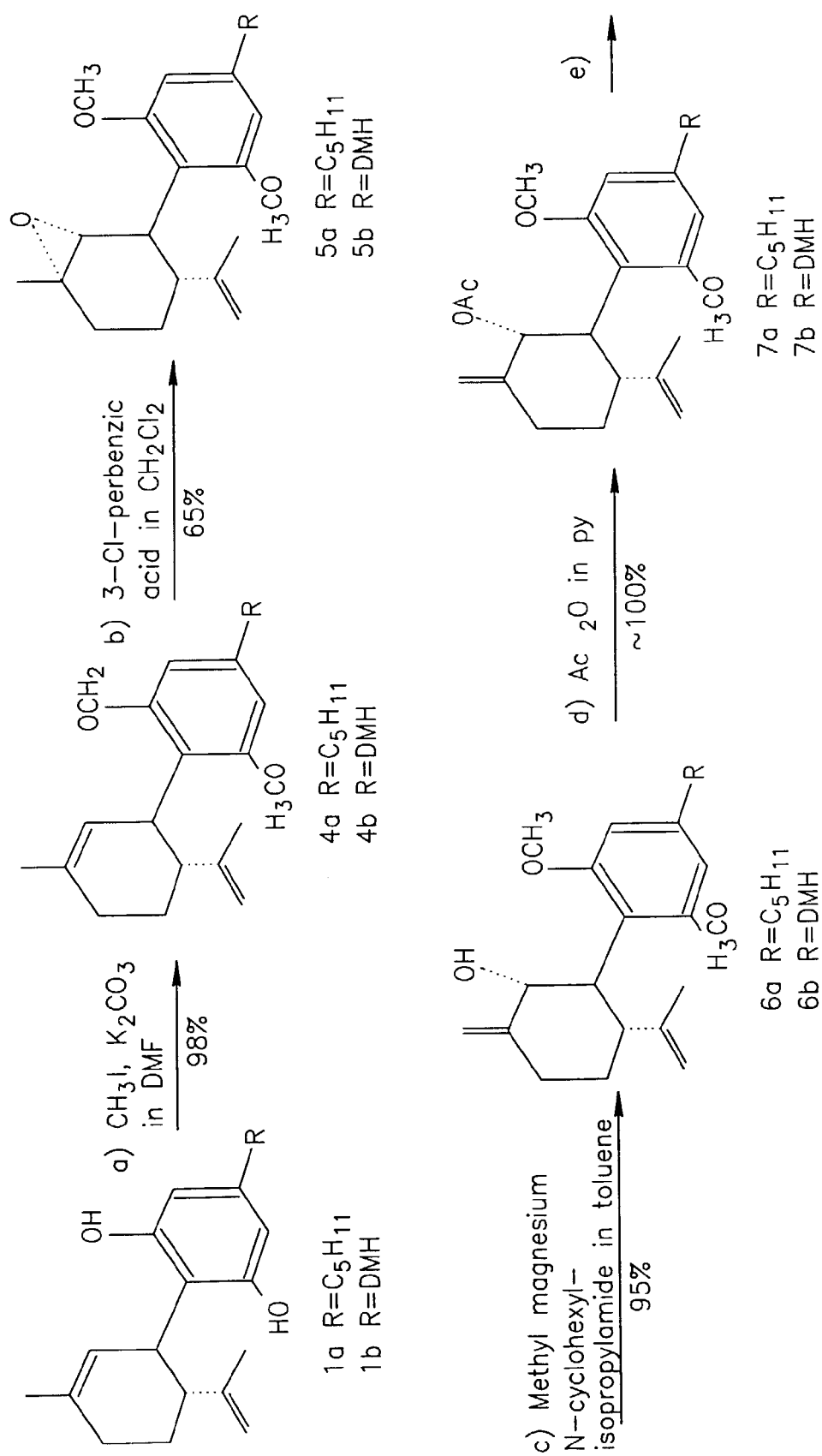
FIG. 3A and FIG. 3B illustrate a procedure for the synthesis of compounds of general Formula.
Figure 3B:
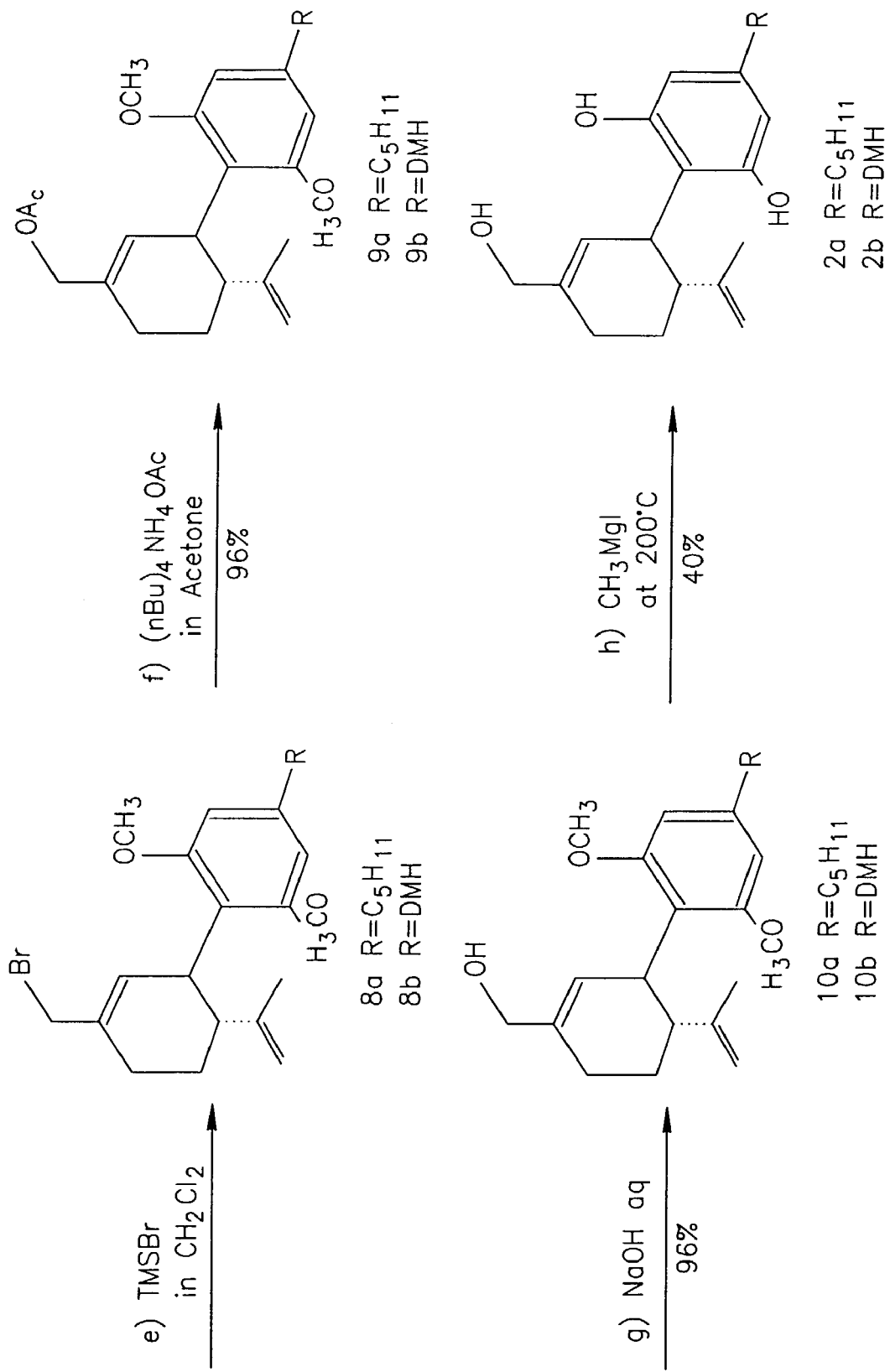

The process for the preparation of compounds of general formula I in which R'=COOH and R"=
a. straight or branched alkyl of 5 to 12 carbon atoms;
b. a group —O—R''', where R''' is straight or branched alkyl to 5 to 9 carbon atoms, or a straight or branched alkyl substituted at the terminal carbon atom by a phenyl group;
c. a group —(CH$_2$)$_n$—O-alkyl, where n is an integer from 1 to 7 and the alkyl group contains 1 to 5 carbon atoms.

involves as starting material an intermediate compound (general formula 6) obtained in the synthesis described in FIGS. 3A and 3B. It is exemplified in FIGS. 3A, 3B and 4, by (6a) in which R"=C$_5$H$_{11}$ or (6b) in which R"=DMH. The first steps involves demethoxylation of the phenolic groups (step a), followed by acetylation (b). The triacetate with general formula (12) can be rearranged and brominated in a single step (c) to yield a bromide (13) which by oxidation (d, e) and hydrolysis (f) leads to the desired compound.

The specific process for the preparation of a compound of general formula I, in which R' stands for COOH and R" stands for C$_5$H$_{11}$ or for DMH comprises:
a. the compound obtained in step d above being reacted with methyl magnesium iodide;
b. the triol obtained being acetylated;
c. the acetylate obtained being rearranged and brominated to obtain the corresponding bromide;
d. the bromide obtained being oxidized with potassium chromate in hexamethylphosphoric triamide;
e. the aldehyde obtained being oxidized with sodium chlorite and reacted with an aqueous solution of sodium hydroxide to obtain the desired compound.

Figure 4:
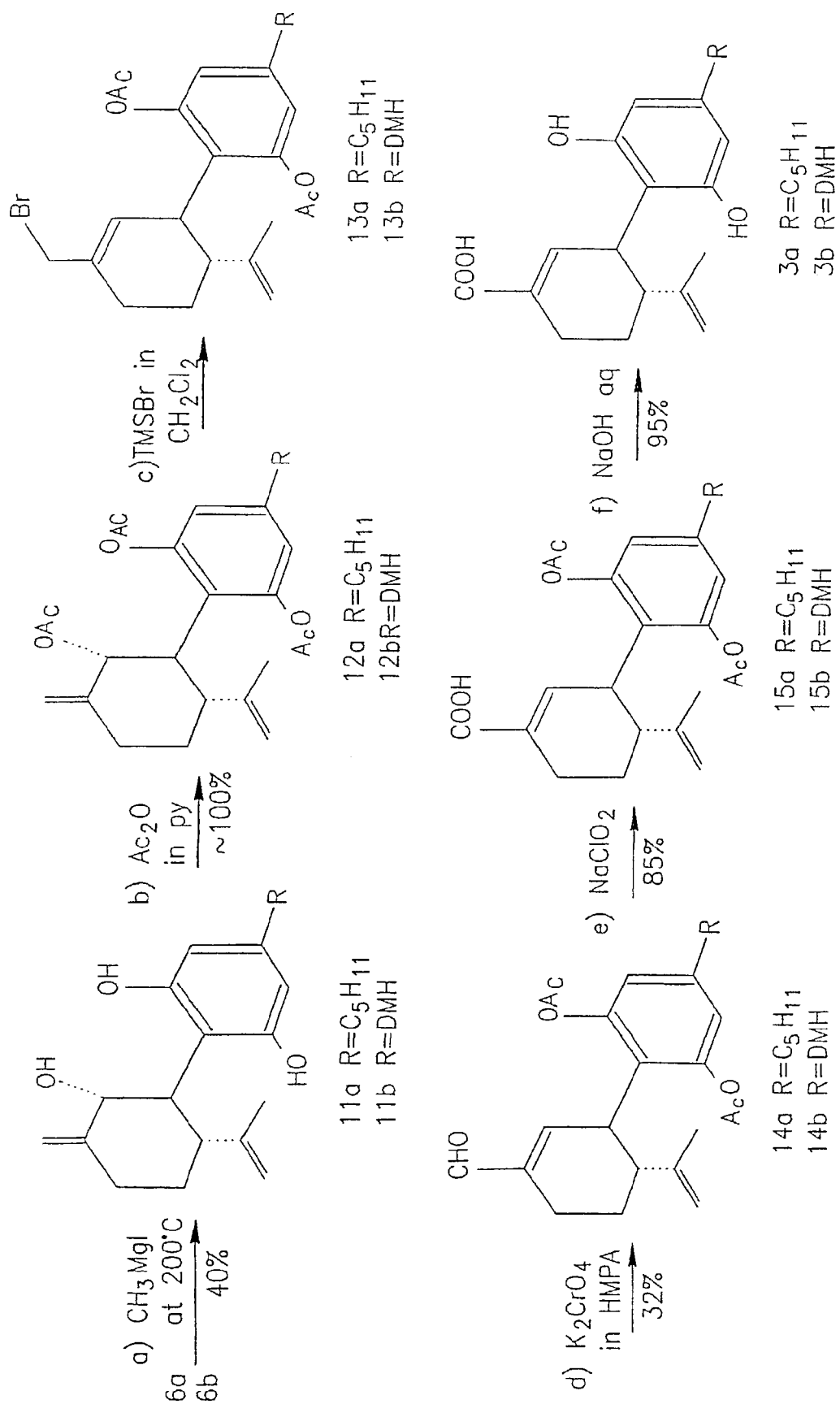
FIG. 4 illustrates a procedure for the synthesis of compounds of general Formula I.

The above specific processes are illustrated in FIGS. 3A, 3B and 4.

Figure 5:
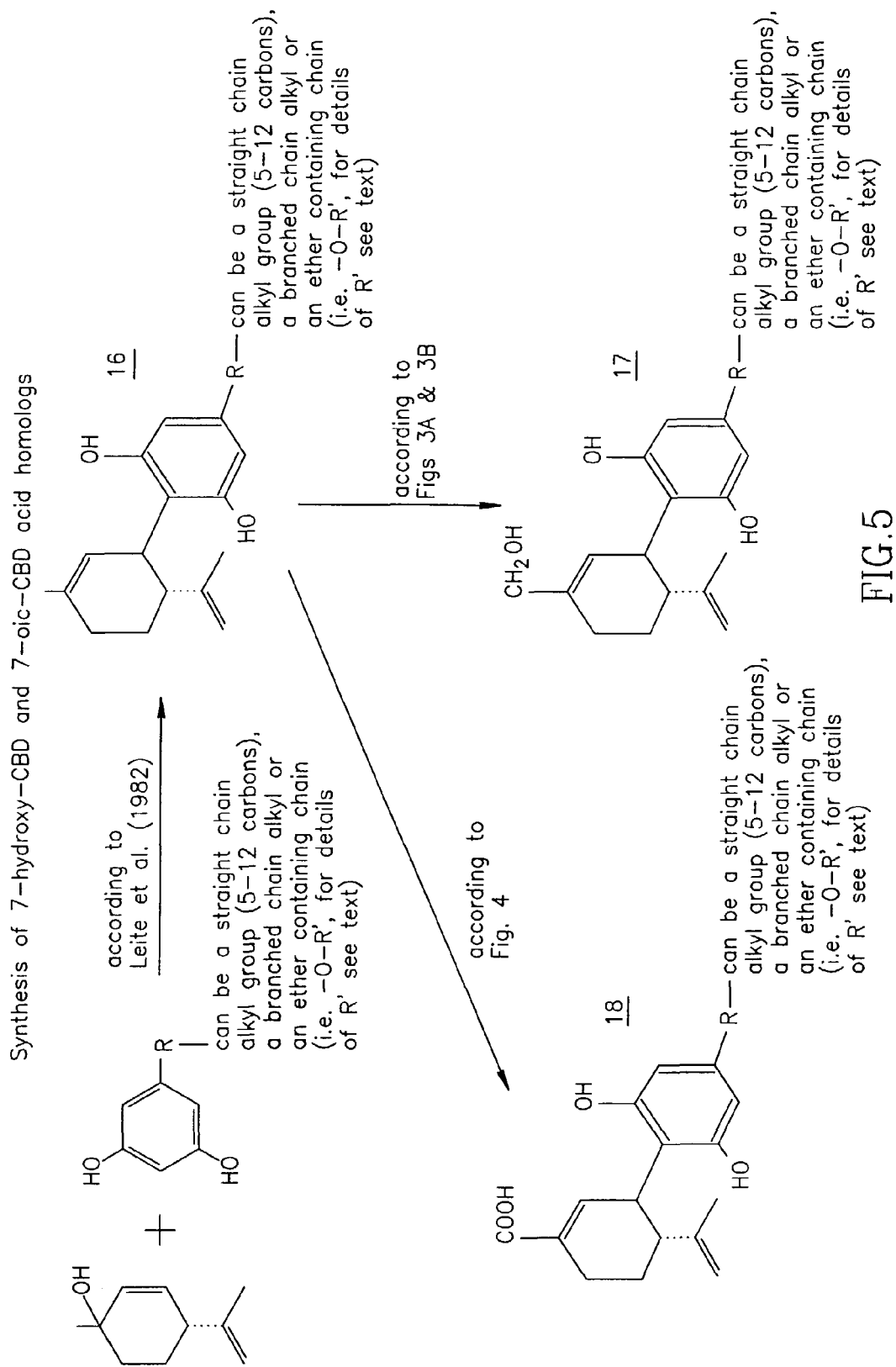
FIG. 5 illustrates a procedure for the synthesis of starting material for the compounds of general Formula I.

The starting material of the compounds of general formula I in which R' stands for CH$_3$ and R" stands for
a. straight or branched alkyl of 5 to 12 carbon atoms;
b. a group —O—R''', where R''' is straight or branched alkyl of 5 to 9 carbon atoms, or a straight or branched alkyl substituted at the terminal carbon atom by a phenyl group;
c. a group —(CH$_2$)$_n$—O-alkyl, where n is an integer from 1 to 7 and the alkyl group contains 1 to 5 carbon atoms.

were prepared of the process exemplified in FIG. 5 in which mentha-2,8-diene-1-ol is condensed with a resorcinol substituted in position 5 (Leite et al.).

The present invention will now be illustrated with reference to the following examples and experiments without being limited by same. The reference to Figures refer to those annexed to the Specification.

I. EXAMPLES

In all the examples, $^1$H NMR spectra were measured on a Varian VXR-300S spectrophotometer using TMS as the internal standard. All chemical shifts are reported in ppm. Specific rotations were detected with a Perkin-Elmer 141 polarimeter. Column chromatography was performed with ICN silica gel 60A. Organic solutions were dried over anhydrous magnesium sulfate.

Example 1

Dimethoxy-CBD (4a)

CBD 1a, (3 g, 9.95 mmol) was dissolved in DMF (55 ml). K$_2$CO$_3$ (7.35 g, 53.3 mmol) and CH$_3$I (2.3 ml, 36.9 mmol) were added and the mixture was stirred at room temperature for 4 hours. The reaction was monitored by TLC (10% Ether/P.E.) till the starting material was disappeared. Then 200 ml of water were added and the solution was extracted with Ether. The organic phase was washed with brine till neutral pH, dried on MgSO$_4$ and filtered. Removal of the solvent under reduced pressure afforded 3.2 g of the product (yield 98%).

(4a): $^1$H-NMR δ 6.344 (2H, s, Ar), 5.220 (1H, s, olefin), 4.460-4.436 (2H, d, J=7.2 Hz), 4.023-3.971 (1H, m, benzyl), 3.741 (6H, s, OCH$_3$), 2.960-2.869 (1H, td, J=11.5, 4.5 Hz, allyl), 2.717-2.569 (2H, t, J=7.5 Hz, benzyl), 2.259-2.144 (1H, m), 2.018-1.960 (1H, m), 1.789-1.722 (1H, m), 1.678 (3H, s, allyl CH$_3$), 1.568 (6H, br s), 1.352 (4H, m) 0.936-0.890 (3H, t, J=6.8 Hz, terminal CH$_3$).

IR: 2875, 1600, 1570, 1440, 1410, 1220, 1100, 880 cm$^{-1}$.

[α]$_D$ −96.8° (c 12.19 mg/ml, CHCl$_3$)

Example 2

Dimethoxy-CBD-DMH (4b)

Prepared with the same procedure reported for (4a), with CBD-DMH as starting material.

(4b): $^1$H-NMR δ 6.449 (2H, s, Ar), 5.238 (1H, s, olefin), 4.422-4.382 (2H, d, J=12.0 Hz), 4.120-3.901 (1H, m, benzyl), 3.784 (6H, s, OCH$_3$), 2.933-2.801 (1H, m, benzyl), 2.270-2.086 (1H, m, allyl), 2.048-1.924 (1H, m), 1.781-1.501 (10H, m), 1.253-1.185 (10H, m), 1.105-0.962 (2H, m) 0.849-0.8816 (3H, t, J=6.8 Hz, terminal CH$_3$).

IR: 2900, 1600, 15780, 1440, 1400, 1100 cm$^{-1}$.

[α]$_D$ −98.1° (c 2.04 mg/ml, CHCl$_3$)

Example 3

1,2 Oxido-dimethoxy-hexahydrocannabinol (5a)

3-Chloro-perbenzoic acid (70% pure 1.2 g, 4.85 mmol) was dissolved in 50 ml CH$_2$Cl$_2$ and the solution was cooled to 0° C. A solution of (4a) (1.65 g, 4.82 mmol) in 10 ml CH$_2$Cl$_2$ was slowly injected. The reaction mixture was stirred at 0° C. for 30 min and monitored by TLC (10% Ether/P.E.). The reaction was quenched by addition of a saturated aqueous solution of NaHCO$_3$ and the organic phase was separated by a separatory funnel, then the aqueous phase was extracted with ether. The combine organic extracts were washed with brine, dried over MgSO$_4$ and filtered. Removal of the solvents under reduced pressure afforded a residue that was flash chromatographed (7% Ether/P.E) to give the epoxy-derivative (5a) (yield 65%).

(5a): $^1$H-NMR δ 6.348-6.322 (2H, d, J=7.7 Hz, Ar), 4.369 (1H, s, olefin), 4.159 (1H, s, olefin), 3.803 (3H, s, OCH$_3$), 3.714 (3H, s, OCH$_3$), 3.612-3.571 (1H, d, J=12.2, Hz, H on epoxide ring), 2.574-2.522 (2H, t, J=7.9 Hz, benzyl), 2.293-2.201 (1H, m), 2.081-1.995 (1H, m), 1.882-1.757 (1H, m), 1.628-1.585 (6H, m), 1.364-1.313 (9H, m), 0.936-0.890 (3H, t, J=6.5 Hz, terminal CH$_3$).

IR: 2900, 1610, 1580, 1460, 1420, 1120, 760 cm$^{-1}$.

Example 4

1,2 Oxidodimethoxyhexahydrocannabinol DMH (5b)

Prepared with the same procedure reported for (5a), but the yield was slightly better (70%).

(5b): $^1$H-NMR δ 6.466-6.442 (2H, d, J=7.2 Hz, Ar), 4.358 (1H, s, olefin), 4.121 (1H, s, olefin), 3.805 (3H, s, OCH$_3$), 3.719 (3H, s, OCH$_3$), 3.591-3.555 (1H, d, J=10.8, Hz, H on epoxide ring), 2.235-2.193 (1H, m, benzyl), 2.105-1.995 (1H, m, allyl), 1.907-1.761 (1H, m), 1.745-1.514 (10H, m), 1.369 (3H, s, allyl CH$_3$), 1.268-1.180 (10H, m), 1.081-0.942 (2H, m.), 0.856-0.812 (3H, t, J=6.5 Hz, terminal CH$_3$).

IR: 2900, 1600, 1580, 1460, 1450, 1210, 1110, 750 cm$^{-1}$.

Example 5

(3R,4R)-3-[2,6-Dimethoxy-4-pentylphenyl]-2-hydroxy-4-isopropenyl-1-methylene cyclohexane (6a)

Butyllithium in hexane (5.6 ml, 14 mmol) was added to a 0° C. solution of N-cyclohexylisopropylamine (1.85 ml, 11.3 mmol) in anhydrous toluene (10 ml, distilled over sodium) under N$_2$ atmosphere. After 15 min, methylmagnesium bromide in ether (3.8 ml, 11.4 mmol) was injected, and the reaction mixture was stirred for 45 min at room temperature. A solution of (5a) (1 g, 2.79 mmol) in dry toluene (3 ml) was added, and the mixture was heated to 40° C. and stirred for two hours. Then the reaction was cooled to 0° C. and quenched by the slow addition of 5M HCl. The organic phase was separated by a separatory funnel, and then the aqueous phase was extracted with ether. The combined organic extracts were washed with brine, dried over MgSO$_4$ and filtered. Removal of the solvents under reduced pressure afforded a residue that on TLC (20% Ether/P.E.) showed only one spot, and by $^1$H-NMR was proved to be (6a) (yield 97%).

(6a): $^1$H-NMR δ 6.332 (2H, s, Ar), 5.083 (1H, s, olefin), 4.821 (1H, s, olefin), 4.662-4.622 (1H, d, J=11.8 Hz, CHOH), 4.387 (1H, s, olefin), 4.379 (1H, s, olefin), 3.798 (3H, s, OCH$_3$), 3.745 (3H, s, OCH$_3$), 3.200-3.154 (1H, td, J=11.2, 3.0 Hz, benzyl), 2.564-2.452 (3H, m), 2.255-1.625 (1H, m), 1.754-1.707 (1H, m), 1.609-1.350 (4H, m), 1.432 (3H, s, allyl CH$_3$), 1.350-1.313 (4H, m), 0.924-0.878 (3H, t, J=6.5 Hz, terminal CH$_3$).

IR: 3400, 2920, 1590, 1450, 1120, 900, 730 cm$^{-1}$.

[α]$_D$ +62.3° (c 15.36 mg/ml, CHCl$_3$)

Example 6

(3R,4R)-3-[4-(1',1' Dimethylheptyl)-2,6-dimethoxyphenyl]-2-hydroxy-4-isopropenyl-1-methylenecyclohexane (6b)

Prepared with the same procedure reported for (6a).

(6b): $^1$H-NMR δ 6.440 (2H, s, Ar), 5.080 (1H, s, olefin), 4.821 (1H, s, olefin), 4.655-4.621 (1H, d, J=9.0 Hz, CHOH), 4.448 (1H, s, olefin), 4.338 (1H, s, olefin) 3.802 (3H, s, OCH$_3$), 3.744 (3H, s, OCH$_3$), 3.215-3.127 (1H, td, J=11.7, 3.0 Hz, benzyl), 2.505-2.444 (1H, dt, J=12.6, 3.0 Hz allyl), 2.255-2.182 (1H, td, J=9.0, 3.0 Hz), 1.740-1.688 (2H, m), 1.555-1.423 (8H, m), 1.301-1.177 (10H, m), 1.025-0.955 (2H, m), 0.859-0.814 (3H, t, J=6.5 Hz, terminal CH$_3$).

IR: 3400, 2900, 1600, 1560, 1450, 1400, 1110, 750 cm$^{-1}$.

[α]$_D$ +47.6° (c 1.05 mg/ml, CHCl$_3$)

Example 7

(3R,4R)-3-[2,6-Dimethoxy-4-pentylphenyl]-2-acetoxy-4 isopropenyl-1-methylenecyclohexane (7a)

(6a) (0.9 g, 2.5 mmol) was dissolved in pyridine (2 ml) and acetic anhydride (2 ml) and the reaction was stirred for 18 hours at room temperature. Then the solution was poured onto iced water (20 ml) and extracted with ether. The combined organic extracts were washed successively with 1N HCl, aqueous sodium bicarbonate and brine, dried on MgSO$_4$ and filtered. Removal of the solvents under reduced pressure afforded an oily residue that on TLC (20% Ether/P.E.) showed only one spot, that by $^1$H-NMR was proved to be (7a) (yield ~100%).

(7a): $^1$H-NMR δ 6.281-6.267 (2H, d, J=4.2 Hz, Ar), 5.967-5.931 (1H, d, J=10.8 Hz, olefin), 4.767-4.721 (2H, d, J=13.7 Hz, olefin), 4.535 (1H, s, olefin), 4.419 (1H, s, olefin), 3.793 (3H, s, OCH$_3$), 3.745 (3H, s, OCH$_3$), 3.491-3.416 (1H, t, J=11.4 Hz), 3.286-3.197 (1H, td, J=11.4, 2.7, Hz, benzyl), 2.533-2.469 (2H, t, J=7.2 Hz), 2.325-2.249 (1H, m), 1.717 (3H, s, OAc), 1.625-1.447 (6H, m), 1.404-1.250 (6H, m), 0.924-0.878 (3H, t, J=6.5 Hz, terminal CH$_3$).

IR: 2910, 1750, 1450, 1360, 1240, 1120, 890 cm$^{-1}$.

Example 8

(3R,4R)-3-[4-(1',1'-Dimethylheptyl)-2,6-dimethoxyphenyl]-2-acetoxy-1-methylenecyclohexane (7b)

Prepared with the same procedure reported for (7a).

(7b): $^1$H-NMR δ 6.409-6.377 (2H, d, J=8.1 Hz, Ar), 5.980-5.931 (1H, d, J=14.5 Hz, CHOAc), 4.768-4.717 (2H, d, J=15.2 Hz, olefin), 4.521 (1H, s, olefin), 4.405 (1H, s, olefin), 3.802 (3H, s, OCH$_3$), 3.754 (3H, s, OCH$_3$), 3.268-3.181 (1H, m, benzyl), 2.522-2.459 (1H, m, allyl), 1.781-1.717 (1H, m), 1.695 (3H, s, OAc), 1.540-1.484 (6H, m), 1.239-1.171 (14H, m), 0.980-0.923 (2H, m), 0.854-0.809 (3H, t, J=6.7 Hz, terminal CH$_3$).

IR: 290, 1750, 1450, 1360, 1240, 1120, 880 cm$^{-1}$.

Example 9

7-Bromo-dimethoxy CBD (8a)

(7a) (1 g, 2.5 mmol) was dissolved in dry CH$_2$Cl$_2$ (50 ml, distilled over CaH$_2$) under nitrogen atmosphere and TMSBr (1.6 ml, 12.1 mmol) was added. The reaction was stirred at r.t. for 4 hours, then it was shaken with a saturated aqueous solution of NaHCO$_3$ and the organic phase was separated by a separatory funnel, then the aqueous phase was extracted with ether. The combine organic extracts were washed with brine, dried over MgSO$_4$ and filtered. Removal of the solvents afforded a residue that $^1$H-NMR and TLC (20% Ether/P.E.) showed predominantly a single component, that was used immediately with no purification.

(8a): $^1$H-NMR δ 6.322 (2H, s, Ar), 5.736 (1H, s, olefin), 4.767 (1H, s, olefin), 4.454), 4.535 (1H, s, olefin), 4.006 (2H, s, CH$_2$Br), 3.736 (6H, s, OCH$_3$), 2.853-2.767 (1H, td, J=11.9, 3.2 Hz, benzyl), 2.565-2.512 (1H, t, J=7.9, Hz, benzyl), 2.397-2.359 (1H, m), 2.277-2.183 (1H, m), 1.870-1.662 (2H, m), 1.619 (3H, s, allyl CH$_3$), 1.439-1.237 (7H, m), 0.928-0.882 (3H, t, J=6.6 Hz, terminal CH$_3$).

IR: 2900, 1580, 1460, 1230, 1120 cm$^{-1}$.

Example 10

7-Bromo-dimethoxy CBD DMH (8b)

Prepared with the same procedure reported for (8a).

(8b): $^1$H-NMR δ 6.431 (2H, s, Ar), 5.602 (1H, s, olefin), 4.821-4.337 (4H, m, CH$_2$Br+olefin), 4.042-3.961 (1H, m, olefin), 3.720 (6H, s, OCH$_3$), 3.116-3.010 (1H, m, benzyl), 2.842-2.762 (1H, allyl), 1.782-1.517 (9H, m), 1.247-1.178 (10H, m), 1.010 (2H, br s), 0.831 (3H, br s, terminal CH$_3$).

IR: 2910, 1580, 1460, 1230, 1120 cm$^{-1}$

Example 11

7-Acetoxy-dimethoxy CBD (9a)

(8a) (570 mg, 1.35 mmol) was dissolved in acetone (15 ml, stored on 4A° molecular sieves) and tetrabutylammonium acetate (450 mg, 1.49 mmol). The mixture was stirred, refluxed and monitored by TLC (20% Ether/P.E.). After 2 hours there was no more starting material. The acetone was removed under reduced pressure, and the residue was diluted with water (20 ml) and extracted with ether. The combine organic extracts were washed with aqueous sodium bicarbonate and brine, dried on MgSO$_4$ and filtered. Removal of the solvents under reduced pressure afforded 520 mg of an oily residue (96% yield).

(9a): $^1$H-NMR δ 6.320 (2H, s, Ar), 5.581 (1H, s, olefin), 4.492-4.386 (4H, m, CH$_2$OAc+olefin), 4.040-3.986 (1H, m, benzyl), 3.715 (6H, s, OCH$_3$), 2.853-2.801 (1H, m), 2.195-2.071 (2H, m), 2.060 (3H, s, OAc), 1.823-1.695 (2H, m), 1.605 (5H, br s), 1.323 (4H, br s), 0.921-0.875 (3H, t, J=6.7 Hz, terminal CH$_3$).

IR: 2900, 1720, 1580, 1440, 1110 cm$^{-1}$.

$[α]_D$ −135.2° (c 15.95 mg/ml, CHCl$_3$)

Example 12

7-Acetoxy-dimethoxy CBD DMH (9b)

Prepared with the same procedure reported for (9a), but the yield was slightly worse (90%).

(9b): $^1$H-NMR δ 6.440 (2H, s, Ar), 5.609 (1H, s, olefin), 4.498-4.343 (4H, m, CH$_2$OAc+olefin), 4.041-3.965 (1H, m, benzyl), 3.719 (6H, s, OCH$_3$), 2.845-2.763 (1H, m, allyl), 2.193-2.099 (2H, m), 2.061 (3H, s, OAc), 1.796-1.776 (2H, m), 1.594-1.518 (7H, m), 1.254-1.179 (10H, m), 1.015 (2H, br s), 0.856-0.861 (3H, t, J=6.4 Hz, terminal CH$_3$).

IR: 2900, 1720, 1600, 1580, 1450, 1410, 1220 cm$^{-1}$.

$[α]_D$ −90.5° (c 2.53 mg/ml, CHCl$_3$)

Example 13

7-Hydroxy-dimethoxy CBD (10a)

(9a) (500 mg, 1.25 mmol) was dissolved in ethanol (20 ml) and NaOH 1N (2 ml) was added and the reaction was refluxed for 1 hour. The ethanol was removed under reduced pressure, and the residue was diluted with water (20 ml) and HCl 2N was added till acid pH. The solution was extracted with ether. The combine organic extracts were washed brine, dried on MgSO$_4$ and filtered. Removal of the solvents under reduced pressure afforded 430 mg of an oily residue (96% yield).

(10a): $^1$H-NMR δ 6.328 (2H, s, Ar), 5.510 (1H, s, olefin), 4.458-4.414 (2H, d, J=13.2 Hz, olefin), 4.010 (2H, br s, CH$_2$OH), 3.728 (6H, s, OCH$_3$), 2.858-2.806 (1H, m, benzyl), 2.566-2.508 (2H, t, J=7.5 Hz, benzyl), 2.213 (2H, m), 1.817-1.582 (7H, m), 1.451-1.259 (5H, m), 0.924-0.878 (3H, t, J=6.5 Hz, terminal CH$_3$).

IR: 3300, 2900, 1580, 1440, 1220, 1110 cm$^{-1}$.

MS m/z (relative intensity): 358 (M$^+$, 7), 327 (52), 290 (80), 221 (100), 152 (33).

Exact mass calculated for C$_{25}$H$_{38}$O$_3$: 358.25080, found 358.2511.

Example 14

7-Hydroxy-dimethoxy CBD DMH (10b)

Prepared with the same procedure reported for (10a).

(10b): $^1$H-NMR δ 6.446 (2H, s, Ar), 5.528 (1H, s, olefin), 4.434-4.367 (2H, d, J=20.1 Hz, olefin), 4.010 (3H, br s, CH$_2$OH+OH), 3.729 (6H, s, OCH$_3$), 2.905-2.785 (1H, m, benzyl), 2.248-2.105 (2H, m), 1.759-1.704 (2H, m), 1.535 (3H, s, allyl CH$_3$), 1.495-1.460 (4H, m) 1.360-1.120 (10H, m) 0.980-0.9875 (2H, m), 0.797-0.752 (3H, t, J=6.5 Hz, terminal CH$_3$).

IR: 3300, 2900, 1600, 1570, 1420, 1400, 1230, 1110, 750 cm$^{-1}$.

$[α]_D$ −135.2° (c 15.95 mg/ml, CHCl$_3$)

MS m/z (relative intensity): 414 (M$^+$, 14), 396 (8), 383 (100), 346 (43), 277 (50), 119 (7).

Exact mass calculated for $C_{27}H_{42}O_3$: 358.31340, found 358.3136.

Example 15

7-Hydroxy CBD (2a)

A Grignard reagent was prepared with magnesium (100 mg, 4.17 mmol) and $CH_3I$ (0.26 ml, 4.17 mmol) in dry ether (3 ml, distilled over sodium) under $N_2$ atmosphere. (10a) (420 mg, 1.17 mmol) in ether (1 ml) was slowly added to the stirred solution and the ether was distilled off. The residue was heated under $N_2$ atmosphere till 210° C. for 45 min. Then the flask was cooled till room temperature and the reaction was quenched with ice water. The aqueous solution was extracted with ether several times. The combine organic extracts were dried on $MgSO_4$ and filtered. Removal of the solvents under reduced pressure afforded a residue that was chromatographed on silica gel (25% Ether/P.E.) to give 150 mg of the pure (2a) (yield 40%).

(2a): $^1$H-NMR δ 6.200 (2H, s, Ar), 5.822 (1H, s, olefin), 4.629 (1H, s, olefin), 4.518 (1H, s, olefin), 4.075 (2H, s, $CH_2OH$), 3.962-3.923 (1H, m, benzyl), 2.567-2.484 (1H, td, J=13.3, 2.7 Hz, allyl), 2.435-2.384 (2H, t, J=7.5 Hz, benzyl), 1.882-1.734 (2H, m), 1.660 (6H, s. allyl $CH_3$), 1.584-1.487 (2H, m), 1.285-1.248 (6H, m), 0.886-0.843 (3H, t, J=6.3 Hz, terminal $CH_3$).

IR: 3300, 2900, 1620, 1580, 1440, 1240, 1020, 730 $cm^{-1}$.

$[α]_D$ −67.3° (c 19.51 mg/ml, $CHCl_3$)

MS m/z (relative intensity): 330 ($M^+$, 10), 312 (44), 299 (53), 284 (44), 244 (100), 231(56), 187 (29), 147 (13).

Exact mass calculated for $C_{21}H_{30}O_3$: 330.21949, found 330.2231.

Example 16

7-Hydroxy CBD-DMH (2b)

Prepared with the same procedure reported for (2a).

(2b): $^1$H-NMR δ 6.335 (2H, s, Ar), 5.863 (1H, s, olefin), 4.652 (1H, s, olefin), 4.538 (1H, s, olefin), 4.108 (2H, s, $CH_2OH$), 3.920-3.889 (1H, d, J=9.3 Hz, benzyl), 2.498-2.433 (1H, m, allyl), 2.228 (2H, br s), 2.064-1.715 (2H, m), 1.648-1.428 (7H, m), 1.312-1.168 (12H, m), 0.853-0.808 (3H, t, J=6.5 Hz, terminal $CH_3$).

IR: 3300, 2900, 1620, 1580, 1420, 1210, 1020, 750 $cm^{-1}$.

$[α]_D$ −61.1° (c 1.8 mg/ml, $CHCl_3$)

MS m/z (relative intensity): 386 ($M^+$, 24), 369 (30), 368 (30), 355 (100), 300 (43), 287 (510), 283 (34), 249 (38), 233 (22), 187 (10).

Exact mass calculated for $C_{25}H_{38}O_3$: 386.28210, found 386.2825.

Figure 1:
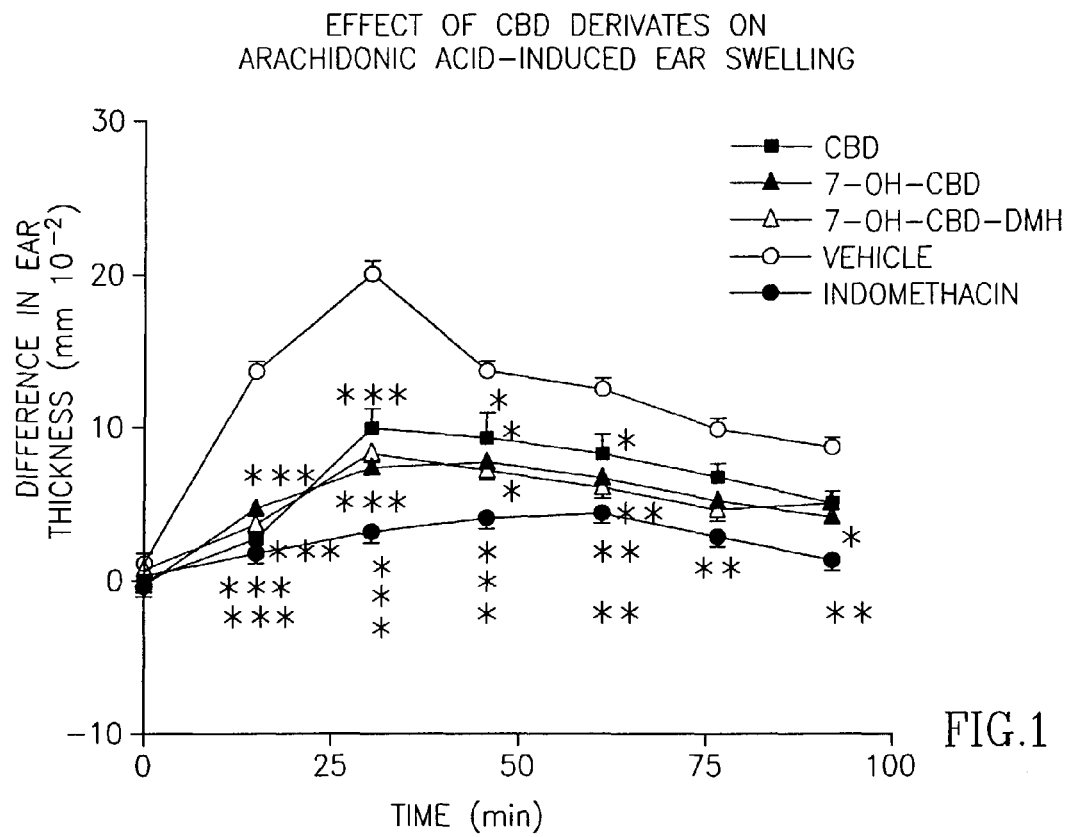
FIG. 1 illustrates the effect of CBD derivatives and indomethacin on arachidonic acid-induced ear swelling.

Effects of CBD (1a), 7-hydroxy-CBD (2a) (Example 15) and of 7-hydroxy-CBD-DMH (2b) (Example 16) and of indomethacin 30 min after arachidonic acid (A'A) induced, as shown in FIG. 1, swelling of the ear. Mice (female Sabra) were treated with 4.5 mg A'A (in 5 μl EtOH) dispersed on the inner surface of one of the ears. The other ear was treated with 5 μl of EtOH. Ear swelling was assessed by measuring ear thickness with a dial thickness gauge (Mitutoyo, Japan) just before treatment and 30 min after A;A application. The drugs (40 mg/kg for the cannabinoids and 20 mg/kg for indomethacin) were injected i.p. 60 min before the A'A treatment. *** indicates p<0.001.

Example 17

(3R,4R)-3-[2,6-Dihydroxy-4-pentylphenyl]-2-hydroxy-4-isopropenyl-1-methylene cyclohexane (11a)

A Grignard reagent was prepared with magnesium (84 mg, 3.5 mmol) and $CH_3I$ (0.2 ml, 3.5 mmol) in dry ether (1 ml, distilled over sodium) under $N_2$ atmosphere. (6a) (360 mg, 1 mmol) in ether (0.5 ml) was added to the stirred solution and the ether was distilled. The residue was heated under $N_2$ atmosphere till 210° C. for 45 min. Then the flask was cooled till room temperature and the reaction was quenched with ice water. The aqueous solution was extracted several times with ether. The combined organic extracts were dried on $MgSO_4$ and filtered. Removal of the solvents under reduced pressure afforded a residue that was chromatographed on silica gel (25% Ether/P.E.) to give 132 mg of the pure (11a) (yield 40%).

(11a): $^1$H-NMR δ 6.156-6.097 (2H, d, J=17.7 Hz, Ar), 5.612 (1H, s, OH), 5.370 (1H, s, OH), 5.092 (1H, s, olefin), 4.847 (1H, s, olefin), 4.684-4.625 (2H, m, CHOH+olefin), 4.462 (1H, s, olefin), 3.300-3.205 (1H, td, J=12.7, 2.7 Hz, benzyl), 3.128-3.058 (1H, t, J=10.5, Hz, allyl), 2.270-2.141 (1H, m), 2.122-2.049 (1H, br s, OH), 1.767-1.712 (1H, m), 1.534-1.48 (5H, m), 1.290-1.183 (4H, m), 0.895-0.881 (3H, t, J=6.6 Hz, terminal $CH_3$).

IR: 3350, 2900, 1620, 1580, 1420, 1160, 1000, 750 $cm^{-1}$.

Example 18

(3R,4R)-3-[4-(1',1'-Dimethylheptyl)-2,6-dihydroxyphenyl]-2-hydroxy-4-isopropenyl-1-methylenecyclohexane (11b)

Prepared with the same procedure reported for (11a), but the yield was slightly better (45%).

(11b): $^1$H-NMR δ 6.295 (1H, s, Ar), 6.229 (1H, s, Ar), 5.786 (1H, s, OH), 5.546 (1H, s, OH), 5.127 (1H, s, olefin), 4.861 (1H, s, olefin), 4.751-4.716 (1H, d, J=3.3 Hz, CHOH), 5.127 (1H, s, olefin), 4.444 (1H, s, olefin), 3.421-3.276 (1H, m, benzyl), 3.132-3.062 (1H, t, J=10.5, Hz, allyl), 2.502-2.459 (1H, d, J=12.9 Hz), 2.251-2.175 (2H, m), 1.780-1.739 (1H, m), 1.528 (3H, s, allyl $CH_3$) 1.460-1.433 (4H, m), 1.251-1.170 (10H, m), 0.954 (2H, br s) 0.845 (3H, br s, terminal $CH_3$).

IR: 3300, 2900, 1620, 1580, 1410, 1210, 750 $cm^{-1}$.

$[α]_D$ +47.3° (c 1.48 mg/ml, $CHCl_3$)

Example 19

(3R,4R)-3-[2,6-Diacetoxy-4-pentylphenyl]-2-acetoxy-4-isopropenyl-1-methylenecyclohexane (12a)

(11a) (100 mg, 0.3 mmol) was dissolved in pyridine (0.5 ml) and acetic anhydride (0.5 ml) and the reaction was stirred for 18 hours at room temperature. Then the solution was poured onto iced water (10 ml) and extracted with ether. The combine organic extracts were washed successively with 1N HCl, aqueous sodium bicarbonate and brine, dried on $MgSO_4$ and filtered. Removal of the solvents under reduced pressure afforded 136 mg of an oily residue that by NMR was proved to be (12a) (yield ~100%).

(12a): $^1$H-NMR δ 6.861 (1H, s, Ar), 6.696 (1H, s, Ar), 5.725-5.688 (1H. d, J=11.1 Hz, CHOAC), 4.083 (1H, s, olefin), 4.689 (1H, s, olefin), 4.540-4.515 (2H, d, J=7.5 Hz, olefin), 3.180-3.105 (1H, t, J=11.3 Hz, benzyl), 2.893-2.802 (1H, td, J=11.3, 3.2 Hz, allyl), 2.563-2.513 (2H, t, J=7.5, Hz, benzyl), 2.374 (3H, s, OAc), 2.280 (3H, s, OAc), 1.798 (3H, s, OAc), 1.614-1.470 (5H, m), 1.286-1.246 (8H, m), 0.886-0.844 (3H, t, J=6.3 Hz, terminal $CH_3$).

IR: 2910, 1750, 1410, 1350, 1180, 1130, 890 $cm^{-1}$.

Example 20

(3R,4R)-3-[2,6-Diacetoxy-4-(1',1'dimethylheptyl)phenyl]-2-acetoxy-4-isopropenyl-1-methylenecyclohexane (12e)

Prepared with the same procedure reported for (12a).

(12b): $^1$H-NMR δ 6.947 (1H, s, Ar), 6.795 (1H, s, Ar), 5.732-5.695 (1H, d, J=11.0 Hz, CHOAC), 4.798 (1H, s, olefin), 4.691 (1H, s, olefin), 4.540-4.515 (2H, d, J=7.5 Hz, olefin), 3.167-3.095 (1H, t, J=11.3 Hz, benzyl), 2.854-2.816 (1H, m, allyl), 2.561-2.515 (1H, d, J=13.8, Hz, benzyl), 2.372 (3H, s, OAc), 2.287 (3H, s, OAc), 2.230-2.195 (1H, m), 1.825-1.770 (4H, m), 1.538-1.424 (6H, m), 1.224-1.151 (12H, m), 0.955-0.945 (2H, m) 0.840-0.799 (3H, t, J=6.1 Hz, terminal $CH_3$).

IR: 2900, 1750, 1410, 1360, 1180, 1130, 890 $cm^{-1}$.

Example 21

7-Bromo-diacetate CBD (13a)

(12a) (100 mg, 0.2 mmol) was dissolved in dry $CH_2Cl_2$ (10 ml, distilled over $CaH_2$) under nitrogen atmosphere. TMSBr (0.13 ml, 1 mmol) and $ZnI_2$ (3.4 mg, 0.01 mmol) were added. The reaction was stirred at r.t. for 4 hours, then it was shaken with a saturated aqueous solution of $NaHCO_3$ and the organic phase was separated by a separatory funnel, then the aqueous phase was extracted with ether. The combined organic extracts were washed with brine, dried over $MgSO_4$ and filtered. Removal of the solvents afforded a residue that was used immediately with no purification.

(13a): $^1$H-NMR δ 6.764 (2H, s, Ar), 5.456 (1H, s, olefin), 4.901 (1H, s, olefin), 4.752 (1H, s, olefin), 3.930-3.903 (2H, m, $CH_2Br$), 3.784-3.756 (1H, d, J=8.2 Hz, benzyl), 2.592-2.643 (2H, m,), 2.306 (6H, s, OAc), 2.198-2.131 (2H, t, J=10.2 Hz), 1.708 (3H, s, allyl $CH_3$), 1.698-1.472 (4H, m), 1.439-1.194 (5H, m), 0.090-0.865 (3H, t, J=5.3 Hz, terminal $CH_3$).

IR: 2900, 1750, 1360, 1200, 1020, 900, 720 $cm^{-1}$.

Example 22

7-Bromo-diacetate CBD DMH (13b)

Prepared with the same procedure reported for (13a).

(13b): $^1$H-NMR δ 6.816 (2H, s, Ar), 5.645 (1H, s, olefin), 4.557 (1H, s, olefin), 4.448 (1H, s, olefin), 4.016-3.966 (2H, m, $CH_2Br$), 3.483-3.405 (1H, m, benzyl), 2.655-2.459 (1H, m, allyl), 2.220 (6H, s, OAc), 1.883-1.637 (4H, m), 1.510 (3H, s, allyl $CH_3$), 1.485-1.426 (4H, m), 1.410-1.176 (10H, m), 1.010-0.995 (2H, m) 0.853-0.807 (3H, t, J=6.5 Hz, terminal $CH_3$).

IR: 2900, 1750, 1370, 1220, 1020, 900, 750 $cm^{-1}$.

Example 23

7-Nor-formyl-diacetate CBD (14a)

(13a) (100 mg, 0.21 mmol), 18-Crown-16 (55.4 mg, 0.21 mmol) and $K_2CrO_4$ (50.9 mg, 0.26 mmol) were dissolved in anhydrous HMPT (2 ml, distilled under vacuum and stored over 4A° molecular sieves). The mixture was stirred and heated at 110° C. for 2 hours. The reaction was cooled and quenched by addition of 1M HCl and the aqueous phase was extracted with ether. The organic phase was washed with brine, dried over $MgSO_4$ and filtered. Removal of the solvent under reduced pressure afforded a residue that was chromatographed on silica gel (20% Ether/PE.) to give 27.7 mg of the pure (14a) (yield 32%).

(14a): $^1$H-NMR δ 9.434 (1Hs CHO), 6.778 (2H, s, Ar), 6.638 (1H, s, olefin), 4.633 (1H, s, olefin), 4.489 (1H, s, olefin), 3.746-3.718 (1H, d, J=8.4 Hz, benzyl), 2.686-2.552 (4H, m), 2.304-2.075 (6H, br s), 1.965-1.921 (1H, m), 1.754-1.590 (6H, m), 1.318-1.305 (5H, m), 0.909-0.865 (3H, t, J=6.2 Hz, terminal $CH_3$).

IR: 2900, 1750, 1670, 1160, 1020 $cm^{-1}$.

$[α]_D$ –111.5° (c 3.5 mg/ml, $CHCl_3$)

Example 24

7-Nor-formyl-diacetate CBD DMH (14b)

Prepared with the same procedure reported for (14a), but the yield was slightly worse (28%).

(14b): $^1$H-NMR δ 9.420 (1Hs CHO), 6.861 (2H, s, Ar), 6.501 (1H, s, olefin), 4.611 (1H, s, olefin), 4.455 (1H, s, olefin), 3.705-3.671 (1H, m, benzyl), 2.667-2.552 (3H, m), 2.292-2.071 (6H, br s, OAc), 1.960-1.890 (2H, m), 1.601 (3H, s, allyl $CH_3$), 1.590-1.485 (4H, m), 1.241-1.711 (8H, m) 1.100-0.931 (2H, m) 0.854-0.865 (3H, t, J=5.7 Hz, terminal $CH_3$).

IR: 2900, 1750, 1660, 1160, 1020 $cm^{-1}$.

$[α]_D$ –85.7° (c 1.4 mg/ml, $CHCl_3$)

Example 25

7-Nor-carboxy-diacetate CBD (15a)

$NaClO_2$ (80% pure 82.6 mg, 0.73 mmol) was added in small quantities to a stirred mixture of (14a) (70 mg, 0.17 mmol), 2-Methyl-2-butene (0.45 ml, 4.25 mmol), a saturated aqueous solution of $KH_2PO_4$ (0.2 ml) in t-Butanol (4 ml). The reaction was stirred at room temperature for 5 hours, and monitored by TLC (50% Ether/P.E.). Then water was added (20 ml) and the mixture was extracted several times with Ethyl Acetate. The organic phase was washed with brine, dried over $MgSO_4$ and filtered. Removal of the solvent under reduced pressure afforded a residue that was chromatographed on silica gel (30% Ether\PE.) to give 61.8 mg of the (15a) (yield 85%).

(15a): $^1$H-NMR δ 6.939 (1H, s, olefin), 6.770 (2H, s, Ar), 4.611 (1H, s, olefin), 4.462 (1H, s, olefin), 3.618-3.718 (1H, m, benzyl), 2.589-2.538 (3H, m, allyl+benzyl), 2.212 (6H, s, OAc), 1.961-1.862 (1H, m), 1.858-1.641 (1H, m), 1.592 (5H, br s), 1.321-1.255 (7H, m), 0.903-0.858 (3H, t, J=6.8 Hz, terminal $CH_3$).

IR: 3300, 2900, 1750, 1270, 1020 $cm^{-1}$.

Example 26

7-Nor-carboxy-diacetate CBD DMH (15b)

Prepared with the same procedure reported for (15a).

(15b): $^1$H-NMR δ 6.946 (1H, s, olefin), 6.854 (2H, s, Ar), 4.592 (1H, s, olefin), 4.436 (1H, s, olefin), 3.635-3.590 (1H, m, benzyl), 2.605-2.455 (1H, m, allyl), 2.208 (6H, s, OAc), 1.950-1.803 (2H, m), 1.795-1.610 (2H, m), 1.574 (3H, s, hhallyl $CH_3$), 1.529-1.475 (4H, m), 1.267-1.174 (10H, m), 1.022 (2H. br s), 0.845-0.805 (3H, t, J=6.6 Hz, terminal $CH_3$).

IR: 3300, 2900, 1750, 1270, 1020 $cm^{-1}$.

Example 27

7-Nor-carboxy CBD (3a)

(15a) (50 mg, 0.12 mmol) was dissolved in ethanol (10 ml) and 1N NaOH (0.5 ml) was added and the reaction was refluxed for 1 hour. The ethanol was removed under reduced pressure, and the residue was diluted with water (20 ml) and the mixture was acidified with 2N HCl. The solution was extracted with ether. The combine organic extracts were washed brine, dried on $MgSO_4$ and filtered. Removal of the solvents under reduced pressure afforded a residue that was chromatographed on silica gel (30% Ether\PE.) to give 38.2 mg of the (3a) (yield 95%).

(3a): $^1$H-NMR δ 7.085 (1H, s, olefin), 6.173 (2H, s, Ar), 4.604-4.566 (2H, d, J=11.4 Hz, olefin), 4.115-4.033 (1H, m, benzyl), 2.799-2.688 (1H, m, allyl), 2.623-2.541 (1H, m), 2.444-2.391 (2H, t, J=7.5 Hz), 1.950-1.869 (1H, m), 1.803-1.669 (5H, m), 1.623-1.453 (4H, m), 1.309-1.178 (5H, m), 0.902-0.857 (3H, t, J=6.5 Hz, terminal $CH_3$).

IR: 3350, 2950, 1700, 1440, 1400, 1160, 920, 740 $cm^{-1}$.

$[α]_D$ –112.3° (c 1.87 mg/ml, MeOH)

Example 28

7-Nor-carboxy CBD DMH (3b)

Prepared with the same procedure reported for (3a).

(3b): $^1$H-NMR δ 7.121 (1H, s, olefin), 6.291 (2H, s, Ar), 4.619-4.555 (2H, d, J=19.1 Hz, olefin), 4.036-4.033 (1H, d, J=8.9 Hz, benzyl), 2.718-2.567 (2H, m), 2.378-2.274 (1H, m), 1.948-1.904 (1H, m), 1.828-1.765 (1H, m), 1.648 (3H, s, allyl $CH_3$) 1.622-1.430 (4H, m), 1.236-1.189 (8H, m), 1.001-0.965 (2H, m), 0.878-0.837 (3H, t, J=6.2 Hz, terminal $CH_3$).

IR: 3330, 2900, 1700, 1420, 1160, 920, 740 $cm^{-1}$.

$[α]_D$ –86.7° (c 2.05 mg/ml, $CHCl_3$)

Figure 2A:
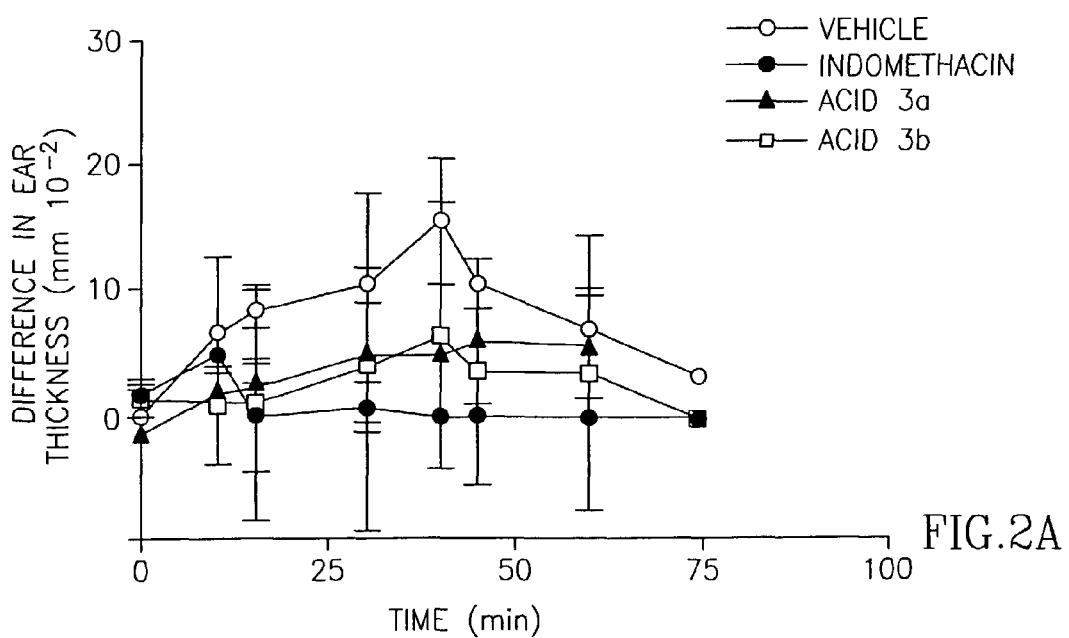
In FIG. 2A, the cannabinoid dose was 80 mg/kg and the indomethacin does was 20 mg/kg.
Figure 2B:
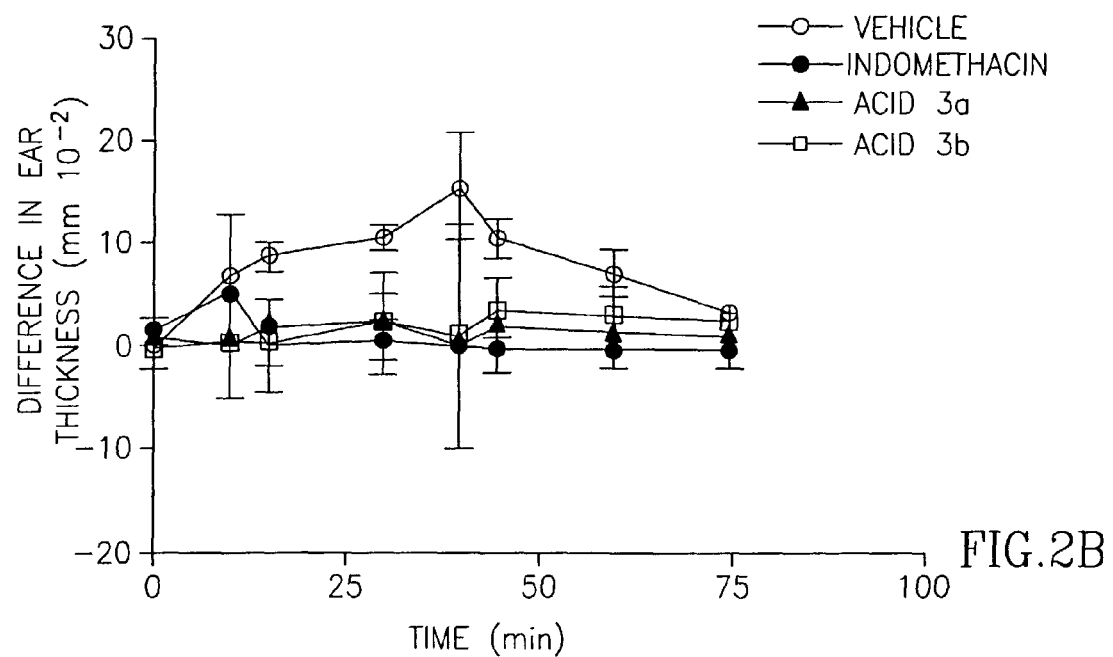
In FIG. 2B, the cannabinoid dose was 40 mg/kg and the indomethacin does was 20 mg/kg.
Figure 2C:
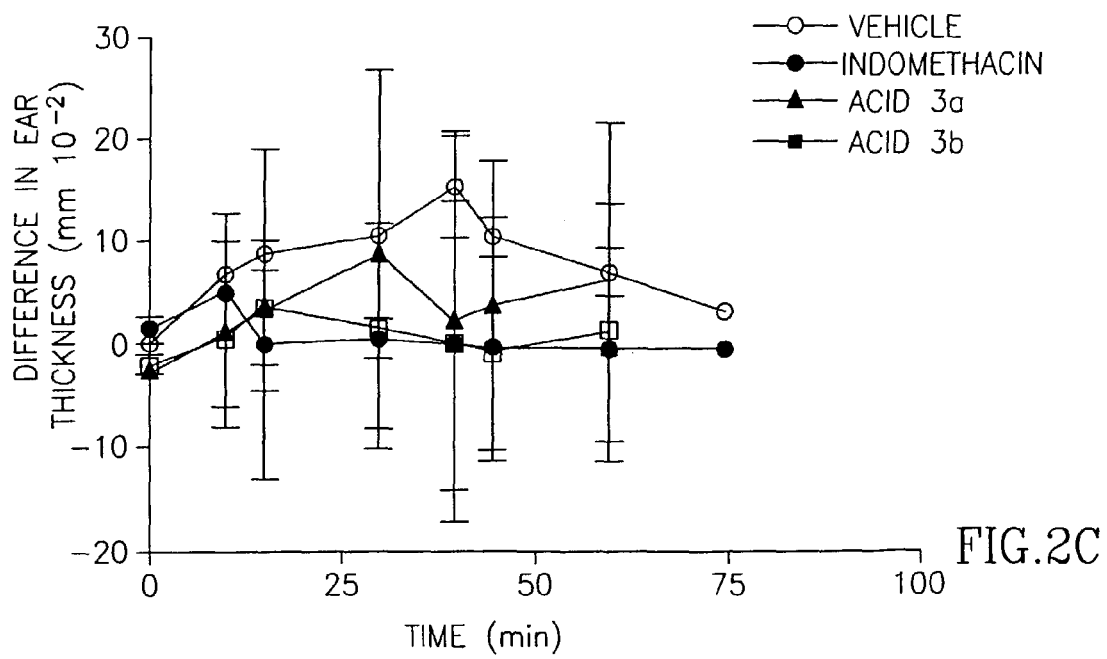
In FIG. 2C, the cannabinoid dose was 5 mg/kg and the indomethacin does was 20 mg/kg.

The effect of various doses of CBD-7-oic acid (3a) (Example 28), and of CBD-DMH-7-oic acid (3b) (Example 28) and of indomethacin (20 mg/kg) after arachidonic acid-induced swelling of the ear are shown in FIG. 2. The effects were measured over 75 min after the administration of arachidonic acid. The experimental details are identical to those described for the testing of CBD (1a) and derivatives thereof.

\*\*\* indicates p<0.001; \*\* p<0.01; \*p<0.05.

A. Cannabinoid dose 80 mg/kg; indomethacin 20 mg/kg

B. Cannabinoid dose 40 mg/kg; indomethacin 20 mg/kg

C. Cannabinoid dose 5 mg/kg; indomethacin 20 mg/kg

II. Pharmacological Activity

Antiinflammatory Activity

The results presented in FIGS. 1, 2 indicate that the CBD metabolites 2a and 3a, as well as their dimethylheptyl homologs 2b and 3b are antiinflammatory. FIG. 1 shows that the results with 2a and 2b significantly differ from those with the control solution. However both compounds (at 40 mg/kg) are less active than the potent antiinflammatory drug indomethacin (at 20 mg/kg). FIG. 1 also indicates that the antiinflammatory effects of 2a and 2b (at 40 mg/kg), although lower than those of indomethacin (at 20 mg/kg), parallel its action for at least about 90 min.

It has previously been shown that some cannabinoids exhibit biphasic effects in various assays (Sulcova et al., Pharmacol. Biochem. Behav. 59, 1998). Hence we looked at the antiinflammatory effects of 3a and 3b over a wide range of doses (FIG. 2). The effect of the acids at 40 mg/kg, i.p. was found to be essentially equivalent to that of indomethacin (20 mg/kg, i.p.). Both 3a and 3b at 80 mg/kg were less effective than indomethacin (20 mg/kg). However at 5 mg/kg, 3b fully suppressed the inflammation and was comparable to indomethacin (20 mg/kg). Compound 3a was less active than 3b at 5 mg/kg.

In another line of experiments it was found that the above described compounds in particular cannabidiol-7-oic acid (15a) and cannabidiol-DMH-7-oic acid (15b) inhibit in vitro up to 90% TNFα production by murine macrophages and by the monocytic cell line RAW 264.7. The inhibition is dose dependent (10 μg-0.001 μg/ml). Tables of results are attached in following Tables A and B.

TABLE A

Effect of cannabidiol-DMH-7-oic acid on TNFα production by (A) Thioglycollate-elicited macrophages (TGMMΦ) and (B) RAW 264.7 mouse monocytic cell line.

| A. TGMΦ | TNFα Titer (S50) After 24 hrs. | | |
|---|---|---|---|
| Agent | Dose μg/ml | S50 | % inhibition |
| LPS |  | 629 |  |
| LPS + HU-320\* | 10 | 159 | 81 |
| LPS + HU-320\* | 5 | 406 | 51 |
| LPS + HU-320\* | 1 | 501 | 40 |
| LPS + HU-320\* | 0.01 | 535 | 36 |

A representative experiment of 6 performed.
\*HU-320 is the code name for cannabidiol-DMH-7-Oic acid (15b in FIG. 4).

TABLE B

| | TNFα Titer. | | |
|---|---|---|---|
| Agent | Dose μg/ml | S50 | % inhibition |
| LPS + HU-320\* | 10 | 615 | 91 |
| | 4 | 2300 | 65 |
| | 1 | 2384 | 63 |
| | 0.1 | 357.6 | 45 |
| | 0.01 | 5818 | 11 |
| LPS | | 6543 | |

\*HU-HU-320 is the code name for cannabidiol-DMH-7-oic acid (15b in FIG. 4).

This anti TNFα effect is also seen in vivo. High levels of TNFα appear in serum of mice after ip injection of 5 mg/kg/mouse lipopolysaccharide (LPS). Administration of cannabidiol-DMH-7-oic acid (15b) in 2 different doses 0.5 and 5 mg/kg simultaneously with LPS, suppressed serum TNFα level. At the lower dose of 0.5 mg/kg 80% suppression of TNFα level was observed. The same effect was observed with other compounds described herewith. Thus 7-hydroxy-CBD (2a) in doses of 10 μg/kg i.p. suppressed serum TNFα in mice (30%).

The above compounds in particular 7-hydroxy-cannabidiol (2a) and 7-hydroxy-cannabidiol-DMH (2b) also inhibit markedly nitric oxide (NO) generation by murine macrophages (up to 90%).

Oxygen radicals intermediate (ROI) generation by macrophages, assayed by chemiluminescence, demonstrated almost total inhibition (up to 95%) when the cells were incubated with cannabidiol-7-oic acid (15a) and cannabidiol-DMH-7-oic acid (15b). Table of results are attached in following Table C.

TABLE C

HU-320 and HU-319 inhibit Zymusan-induced release of reactive oxygen intermediates by monocytic RAW 264.7 cells.

| Treatment of RAW | Cherniluminescense peak | Inhibition % |
|---|---|---|
| (1). Zymosan | 8915 | — |
| Zymosan + HU-320* 4 µg/ml | 1524 | 83 |
| Zymosan + HU-320* 10 µg/ml | 432 | 95 |
| (2). Zymosan | 5992 | — |
| Zymosan + HU-319** 4 µg/ml | 4139 | 31 |
| Zymosan + HU-319** 10 µg/ml | 1041 | 83 |

*HU-320 is the code name for cannabidiol-DMH-7-oic acid (15b in FIG. 4)
**HU-319 is our code name for cannabidiol-7-oic acid (15a in FIG. 4)

The experimental methods used have been described in Gallily et al. (Eur. J. Pharmacol. 406, R5-R7, 2000), Avron and Gallily (J. Leukocyte Biol. 57, 264-268, 1995) and Gallily et al. (J. Pharmacol. Exp. Ther. 283, 918-924, 1997).

The above results indicate that 7-hydroxy-CBD (2a) and 7-hydroxy-CBD-DMH (2b) show antiinflammatory activity. The acids 3a and 3b are much more promising, with 3b (at 5 mg/kg) being as potent as indomethacin (at 20 mg/kg). Said acids show also some analgesic activity.

In view of the potent activity of 7-hydroxy-CBD-DMH (2b) and in particular of CBD-DMH-7-oic acid (3b) numerous additional side chain homologs were prepared. They were synthesized according to FIGS. 3A and 3B, the starting resorcinol derivatives being:

5-(1,2-dimethyl heptyl)-resorcinol
5-(1,2-dimethyloctyl) resorcinol
5-(1,2-dimethylhexyl) resorcinol
5-(1,1-dimethyl heptyl) resorcinol
5-(1-ethyl-2-methylpropyl) resorcinol
5-methylnonyl resorcinol
5-(1-methylnonyl) resorcinol
5-(1-methyloctyl) resorcinol
5-(1,2,4-trimethylhexyl) resorcinol
5-(1-ethylheptyl) resorcinol leading to CBD-type compounds derived from compound type 16. These were converted into the respective homologs 17 and 18, following the synthetic FIGS. 3 and 4.

There have also been used 5-substituted resorcinols in which the side-chain contains an ether such as $OCH_3$, $OC_2H_5$, $OC_3H_7(n)$, $OC_4H_9(n)$, $OCH(CH_3)_2$, $OCH(CH_3)C_2H_5$, $OCH_2CH(CH_3)$ etc.

A further group we used was based on 5 substituted resorcinols in which the alkyl group was substituted: O—CH$(CH_3)(CH_2)_4CH_3$

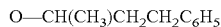

Antinociceptive Activity

It has been found that 2a, 2b, 3a and 3b attenuate the late phase of pain behavior produced by formalin-induced chemical change. Thus mice injected with formalin (3.2% dissolved in saline) licked their paws 8±2 times over 5 min, recorded 30 min after the formalin administration. All four compounds, 2a, 2b, 3a, 3b (20 mg/kg each) fully blocked the licking.

Antianxiety and Anticonvulsive Effects

Preliminary data indicated that in addition to the antiinflammatory and analgesic effects the metabolites 2a and 3a and the homologs 2b and 3b have antianxiety and anticonvulsive effects. Preliminary data also indicate that compounds described herein, such as 1a, 1b, 2a and 2b prevent the uptake of endocannabinoids into neuronal cells and may thus prolong their activity. This action may explain the antianxiety and anticonvulsive activity of these compounds.

Anticancer Effects

It has been found that cannabidiol and other compounds such as cannabidiol-DMH-7-oic acid (15b) described in this specification cause high rate of programmed cell death (apoptosis) in human HL-60 promyelecytic leukemia cells. The apoptosis was cannabinoid dose dependent (0.1 µg/ml to 8 µg/ml). Moreover a very marked synergism reaching up to 85% of apoptosis was seen when HL-60 cells were irradiated by γ ray (800 rad) and treated with cannabidiol and/or other compounds described. The method used, namely determination by the fluorescent Hoechst 33258 stain, is described by T. R. Chen (Cell Res. 104, 255-262, 1977). A Table of results is appended in following Table D.

TABLE D

Apoptosis of HL-60 induced by CBD alone or together with γ-irradiation

| Treatment with canabinoid | % apoptosis | γ-irradiation** + cannabinoid | % apoptosis |
|---|---|---|---|
| (1). Control | 15 | Control | 26 |
| 1 µg/ml CBD | 19 | 1 µg/ml CBD | 28 |
| 4 µg/ml CBD | 33 | 4 µg/ml CBD | 45 |
| 8 µg/ml CBD | 48 | 8 µg/ml CBD | 85 |
| (2). Control | 10 | Control | 15 |
| 5 µg/ml HU-320*** | 15 | 5 µg/ml HU-320 | 25 |
| 10 µg/ml HU-320*** | 27 | 10 µg/ml HU-320 | 58 |

*The cells were incubated with the cannabinoid for 24 h.
**Irradiation (800 rad) by Gammacell 220 Excel
***HU-320 is the code name for cannabidiol-DMH-7-oic acid (15b in FIG. 4).

III Receptor Binding Assays

The $CB_1$ binding assays were performed with synaptosomal membranes prepared from rat brains (Devane et al., 1992). The $CB_2$ assays were performed with transfected cells (Mechoulam et al., 1995). All assays were done in triplicate. The previously described probe [$^3$H]HU-243 was employed in a centrifugation-based ligand binding assay (Devane et al., 1992a, Devane et al., 1992b). It has a $K_i$ value of 45±7 pM.

Animals and Drugs

Female Sabra mice (2 months old, Harlan-Sprague Dawley, Jerusalem) were used for a series of tests and for the assays for inflammation and peripheral pain. Groups of 5 mice were used in each experiment. Compounds 2a, 2b, 3a and 3b were dissolved in vehicle (ethanol:emulphor:saline=1:1:18) and injected intraperitoneally (i.p.) in volumes of 0.1 ml/10 g in mice as previously described (Hanus et al., 1999).

The experiments on animals were performed according to standards determined by the committee on ethics in animal research of the Hebrew University of Jerusalem.

Arachidonic Acid-Induced Ear Inflammation in the Mouse

Ear inflammation was measured by assessing ear tissue swelling after topical application of arachidonic acid. Non-steroidal anti-inflammatory drugs have been shown to reduce swelling in this model (Young et al., 1984). Sixty minutes after i.p. injections of the drug, namely the CBD derivatives or indomethacin, arachidonic acid was applied to the inner surface of one ear (4.5 mg in 5 µl ethanol). The opposite ear served as control (5 µl ethanol). Ear thickness was determined (in 0.01 mm units) every 15 min for 90 min starting immediately after arachidonic acid application using a dial thickness gauge (Mitutoyo, Japan).

Peripheral Pain

Pain mediated by the peripheral nervous system, was tested in the 'formalin test' for cutaneous (peripheral) pain (Tjolson et al., 1992; Calignano et al., 1998; Jaggar et al, 1998). The compound tested (or vehicle) was injected i.p. Formalin (3.2% dissolved in saline) was injected s.c. in the plantar surface of the hind paw of a mouse (in 20 µl volumes) 90 min after the drug. Immediately after formalin administration nociception was assessed (every 5 min for 1 hr) by the number of times the animal licks for formalin-injected paw.

Statistical Analyses

Time curves were compared by two-way analyses-of-variance (ANOVA: time×dose). Differences from vehicle treatments were compared by one-way ANOVA; s, followed by post-hoc Newman-Keuls tests (Prism software from Graph Pad, San Diego).

The invention claimed is:

1. A process for the preparation of a compound-having general Formula I,

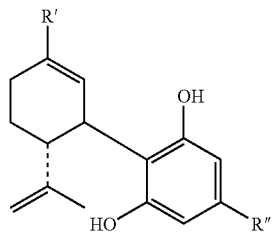

wherein R' is CH$_2$OH and R" is selected from the group consisting of:
  a. a straight or branched alkyl of 5 to 12 carbon atoms;
  b. a group —O—R'", where R'" is a straight or branched alkyl of 5 to 9 carbon atoms, or a straight or branched alkyl substituted at the terminal carbon atom by a phenyl group; and
  c. a group —(CH$_2$)n-O-alkyl, where n is an integer from 1 to 7 and the alkyl group contains 1 to 5 carbon atoms,
the process comprising:
  (a) blocking the phenolic groups of the following compound

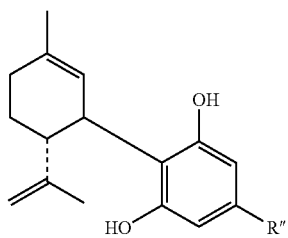

wherein R" is selected from the group above;
  (b) selective epoxidation of the ring double bond of the compound obtained in step (a);
  (c) selective opening of the epoxide ring of the compound obtained in step (b) to form the corresponding allylic alcohol;
  (d) performing an allylic rearrangement of the compound obtained in step (c) to obtain the following compound

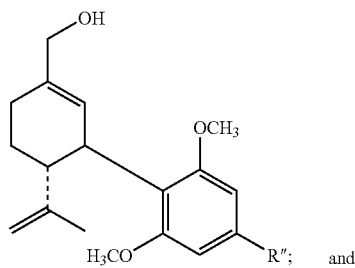

(e) demethoxylating the compound obtained in step (d) to thereby prepare the compound of general formula I.

2. The process according to claim 1, wherein R" is either C$_5$H$_{11}$ or 1',1'-dimethylheptyl (DMH), and wherein:
  in step (a), the phenolic groups are blocked using methyliodide and potassium carbonate in DMF;
  in step (b), the selective epoxidation of the ring double bond is performed using 3-chloroperbenzoic acid;
  in step (c), the selective opening of the epoxide ring is performed using methyl magnesium N-cyclohexyl-isopropylamide in toluene;
  in step (d), the allylic rearrangement of the compound obtained in step (c) is performed by acylating the allylic alcohol formed in step (c), reacting the acylate thus formed with t-butyldimethylsilyl bromide to form the corresponding bromide, reacting the corresponding bromide with (nBu)$_4$NH$_4$OAc in acetone to obtain the allyl acetate diether; and heating the allyl acetate diether in a sodium hydroxide solution; and
  in step (e), the compound obtained in step (d) is demethoxylated using methylmagnesium iodide to thereby obtain the compound of general formula I.

3. A process for the preparation of a compound of general formula I

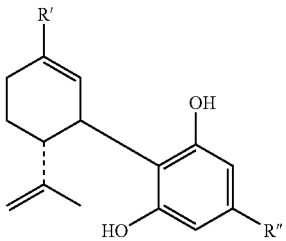

in which R' is COOH, and R" is selected from the group consisting of:
  a. a straight or branched alkyl of 5 to 12 carbon atoms;
  b. a group —O—R'", where R'" is a straight or branched alkyl to 5 to 9 carbon atoms, or a straight or branched alkyl substituted at the terminal carbon atom by a phenyl group; and
  c. a group —(CH$_2$)n-O-alkyl, where n is an integer from 1 to 7 and the alkyl group contains 1 to 5 carbon atoms,
the process comprising:
  (a) demethoxylation of the following compound

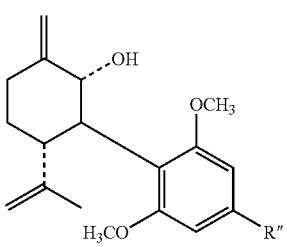

wherein R" is selected from the group above;
  (b) acetylation of the compound obtained in step (a) to form the triacetate;
  (c) rearranging and brominating the triacetate obtained in step (b) to obtain the following compound

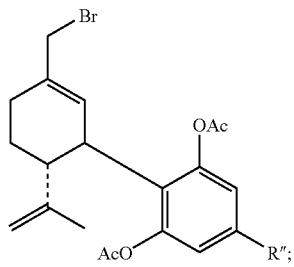

(d) oxidizing the compound obtained in step (c) to obtain the following compound

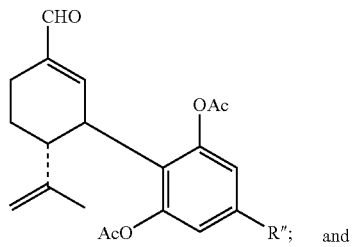
and (e) oxidizing the compound obtained in step (d) and hydrolyzing the product thus formed to thereby obtain the compound of general formula I in which R' is COOH.

4. The process according to claim 3, wherein R" is $C_5H_{11}$ or DMH and wherein:
- in step (a), the compound is demethoxylated with methyl magnesium iodide;
- in step (d), the bromide is oxidized with potassium chromate in hexamethylphosphoric triamide; and
- in step (e), the compound obtained in step (d) is oxidized with sodium chlorite and hydrolyzed with an aqueous solution of sodium hydroxide to thereby obtain the compound of general formula I.

5. A compound having general Formula I

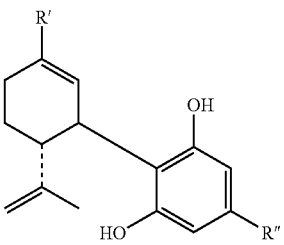

wherein R' is COOH and R" is 1,1-dimethyl heptyl.

* * * * *

UNITED STATES PATENT AND TRADEMARK OFFICE
CERTIFICATE OF CORRECTION

PATENT NO.     : 7,759,526 B2
APPLICATION NO. : 10/311554
DATED          : July 20, 2010
INVENTOR(S)    : Mechoulam et al.

It is certified that error appears in the above-identified patent and that said Letters Patent is hereby corrected as shown below:

Column 1, Line 34: Please correct "[1998])" to read -- [1998] --
        Line 35: Please correct "and "Malfait et al" to read -- and Malfait et al --
        Line 36: Please correct "9566 [2000]."." to read -- 9566 [2000]. --
        Line 38: Please correct "Formukong et al.," to read -- Formukong et al. --
        Line 42: Please correct "an anti-inflammatory assay)"
            to read -- (an anti-inflammatory assay), --

Column 2, Line 67: Please correct "does was" to read -- dose was --

Column 3, Line 1: Please correct "does was" to read -- dose was --
        Line 2: Please correct "indomethacin does" to read -- indomethacin dose --
        Line 5: Please correct "Formula." to read -- Formula I. --
        Line 34: Please correct "which R stands" to read -- which R' stands --
        Line 46: Please correct "diether; and" to read -- diether; --
        Line 55: Please correct "alkyl to 5" to read -- alkyl of 5 --
        Line 57: Please correct "group;" to read -- group; or --
        Line 59: Please correct "carbon atoms." to read -- carbon atoms, --

Column 11, Line 14: Please correct "hexane (12e)" to read -- hexane (12b) --

Column 14, Line 12: Please correct "compounds in" to read -- compounds, in --
        Line 13: Please correct "(15a)" to read -- (3a) --
            and please correct "(15b)" to read -- (3b), --
        Lines 16-17: Please correct "Tables of results are attached in following
            Tables A and B."
            to read -- Results are shown in Tables A and B. --
        Line 32, Table A: Please correct "-7-Oic acid" to read -- -7-oic acid --
            and please correct "(15b in FIG. 4)." to read -- (3b in FIG. 4). --

Signed and Sealed this
Eleventh Day of January, 2011

David J. Kappos
*Director of the United States Patent and Trademark Office*

Line 45: Table B: Please correct "*HU-HU-320" to read -- *HU-320 --
and please correct "(15b in FIG. 4)." to read -- (3b in FIG. 4). --
Line 51: Please correct "acid (15b)" to read -- acid (3b) --
and please correct "doses 0.5" to read -- doses, 0.5 --
Line 52: Please correct "mg/kg simultaneously"
to read -- mg/kg, simultaneously --
Line 53: Please correct "mg/kg 80%" to read -- mg/kg, 80% --
Line 55: Please correct "Thus 7-hydroxy" to read -- Thus, 7-hydroxy --
Line 65: Please correct "acid (15a)" to read -- acid (3a) --
Line 66: Please correct "acid (15b)" to read -- acid (3b) --
Lines 66-67: Please correct "Table of results are attached in following
Table C." to read -- Results are shown in Table C. --

Column 15, Table C, Line 14: Please correct "(15b in FIG. 4)"
to read -- (3b in FIG. 4) --
Line 15: Please correct "is our code" to read -- is the code -- and
please correct "(15a in FIG. 4)"
to read -- (3a in FIG. 4) --
Line 52: Please correct "O-CHCH$_3$)CH$_2$CH$_2$CH$_2$C$_6$H$_5$"
to read -- O-CH(CH$_3$)CH$_2$CH$_2$CH$_2$C$_6$H$_5$ --

Column 16, Line 6: Please correct "(15b)" to read -- (3b) --
Line 7: Please correct "cause high" to read -- cause a high --
Line 8: Please correct "promyelecytic" to read -- promyelocytic --
Lines 14-15: Please correct "A Table of results is appended in following
Table D." to read -- Results are shown in Table D. --
Table D, Line 30: Please correct "(15b in FIG. 4)."
to read -- (3b in FIG. 4). --